United States Patent
Harran et al.

(10) Patent No.: US 8,013,015 B2
(45) Date of Patent: Sep. 6, 2011

(54) SMALL MOLECULE INHIBITORS OF GHRELIN O-ACYLTRANSFERASE

(75) Inventors: Patrcik G. Harran, Los Angeles, CA (US); Michael S. Brown, Dallas, TX (US); Joseph L. Goldstein, Dallas, TX (US); Jing Yang, Dallas, TX (US); Tong-Jin Zhao, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/571,538

(22) Filed: Oct. 1, 2009

(65) Prior Publication Data

US 2010/0086955 A1  Apr. 8, 2010

Related U.S. Application Data

(60) Provisional application No. 61/102,353, filed on Oct. 2, 2008.

(51) Int. Cl.
*A61K 31/505* (2006.01)
*A61K 31/27* (2006.01)
*A61K 31/216* (2006.01)
*A61K 31/165* (2006.01)
*C07D 239/26* (2006.01)
*C07C 275/18* (2006.01)
*C07C 271/22* (2006.01)
*C07C 235/32* (2006.01)

(52) U.S. Cl. ........ 514/489; 514/256; 514/595; 514/588; 514/516; 544/335; 564/56; 564/158; 564/159; 560/125

(58) Field of Classification Search ............. 514/489, 514/256, 595, 588, 516; 544/335; 564/56, 564/158, 159; 560/125
See application file for complete search history.

(56) References Cited

U.S. PATENT DOCUMENTS
2006/0217296 A1 * 9/2006 Jansson .................. 514/12

FOREIGN PATENT DOCUMENTS
JP  60146091 A * 8/1985

OTHER PUBLICATIONS

CAplus record of JP 60146091, 1986.*
Makita et al. Journal of Chromatography 1976, 124, 92-96.*
Makita et al. Journal of Chromatography, 1976, 120, 129-140.*
Matsumoto et al. Biochemical and Biophysical Research Communications 2001, 284, 655-659.*
Hosada et al. Clinical Chemistry 2004, 50, 1077-1080.*
Kojima et al. Physiol Rev. 2005, 85, 495-522.*
Wermuth, C.G. "Molecular Variations Based on Isosteric Replacements" in "The Practice of Medicinal Chemistry" 1996, Academic Press Limited, pp. 203-237.*
Sheridan, R.P. J. Chem. Inf. Comput. Sci. 2002, 42, 103-108.*
Graham et al. Biochemistry 1989, 28, 7889-7895.*
Biel et al. Chem. Eur. J. 2006, 12, 4121-4143.*

* cited by examiner

*Primary Examiner* — Joseph Kosack
*Assistant Examiner* — Matthew Coughlin
(74) *Attorney, Agent, or Firm* — Richard Aron Osman

(57) ABSTRACT

Ghrelin O-acyltransferase (GOAT) is inhibited with designed small molecules. Methods comprise contacting the GOAT with an inhibitor and detecting a resultant inhibition.

24 Claims, No Drawings

SMALL MOLECULE INHIBITORS OF GHRELIN O-ACYLTRANSFERASE

This application claims priority to Ser. No. 61/102,353, filed Oct. 2, 2008.

This work was supported by grants from the National Institutes of Health (HL20948); the Government has certain rights in this invention.

The field of the invention is inhibition of ghrelin O-acyltransferase (GOAT).

INTRODUCTION

Ghrelin O-acyltransferase (GOAT) is the membrane-bound enzyme that attaches 8-carbon octanoate to a serine residue in ghrelin, a peptide hormone. Ghrelin comprises the N-terminal 28 amino acids of proghrelin, a precursor of 94 amino acids that is cleaved proteolytically to release ghrelin. The octanoylated serine is the third amino acid from the N-terminus of ghrelin, and its presence is essential for the physiologic actions of ghrelin in stimulating appetite and other neuroendocrine functions.

Most ghrelin is produced in a minor population of endocrine cells in the gastric mucosa, originally called X/A-like cells and now called ghrelin cells. After secretion into plasma, octanoylated ghrelin travels to the pituitary where it binds to a G protein-coupled receptor that triggers the release of growth hormone. The plasma concentration of ghrelin rises immediately before meals, and the octanoylated peptide enhances food intake when administered to rats and humans. Inactivation of the gene encoding ghrelin or its receptor produces a modest resistance to obesity in mice that are presented with a high fat diet. These observations led to the hypothesis that interference with ghrelin action might protect against obesity in humans.

One way to inhibit ghrelin action would be to inhibit GOAT. The enzyme is an attractive target because ghrelin is the only protein known to be octanoylated, and hence GOAT inhibition is likely to alter only one protein. GOAT was first identified by transfection of candidate cDNAs into cultured endocrine cells that process proghrelin to ghrelin but fail to attach octanoyl. With these transfection assays, the enzyme attached octanoyl to the appropriate serine-3 in ghrelin, and the attachment reaction was shown to require the two amino acids in GOAT (asparagine-307 and histidines-338) that are conserved in other membrane-bound O-acyltransferases. GOAT is a highly hydrophobic protein with eight postulated membrane-spanning helices. It is presumed to be located in the endoplasmic reticulum where proghrelin is initially inserted.

Thus far, the action of GOAT has been studied only in intact cells. In copending U.S. Ser No. 12/167,917, we described a biochemical assay for GOAT activity using membranes from insect cells that express mammalian GOAT as a result of infection with a recombinant baculovirus. Using purified recombinant proghrelin as a substrate, we characterized the enzymatic properties of GOAT, and we showed that the enzyme is potently inhibited by octanoylated peptides that derived from the first five amino acids of ghrelin. Here we disclose the design and synthesis of small molecule GOAT inhibitors.

SUMMARY OF THE INVENTION

The invention provides methods, compounds and compositions for inhibiting ghrelin O-acyltransferase (GOAT). In one embodiment, the invention provides compounds of and pharmaceutical compositions comprising a GOAT inhibitor having the structure 1:

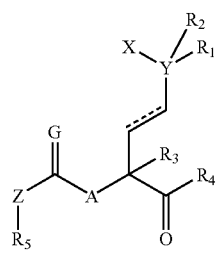

wherein:

$R_1$, is selected from optionally hetero-, optionally substituted (C6-C9) alkyl, optionally hetero-, optionally substituted (C6-C9) alkenyl, and optionally hetero-, optionally substituted (C6-C9) alkynyl;

$R_2$-$R_5$ are independently selected from an electron pair, hydrogen, optionally hetero, optionally substituted alkyl, optionally hetero-, optionally substituted alkenyl, optionally hetero-, optionally substituted alkynyl, optionally hetero-, optionally substituted aryl, and an optionally substituted heteroatom;

A is selected from $CH_2$, O, S, NH, and N-alkyl;

G is selected from O, S, NH, and N-alkyl;

X is selected from hydroxyl, amino, alkylamino, and alkylthio;

Y is selected from C, N, O and S (wherein the X—Y bond encompasses both diastereomers); and Z is selected from $CH_2$, O, S, NH and N-alkyl.

The invention encompasses all alternative combinations of particular embodiments:

wherein $R_1$, is selected from optionally hetero-, optionally substituted hepta-alkyl, optionally hetero-, optionally substituted hepta-alkenyl, and optionally hetero-, optionally substituted hepta-alkynyl;

wherein $R_1$, is selected from hepta-alkyl (heptanyl), hepta-alkenyl (heptenyl), and hepta-alkynyl (heptynyl);

wherein $R_1$, is selected from n-heptanyl, n-heptenyl, and n-heptynyl;

wherein $R_1$, is n-heptanyl;

wherein $R_1$, is n-4-heptenyl (—$CH_2CH_2CH_2CHCHCH_2CH_3$) (E or Z isoform);

wherein $R_1$, is n-4-heptynyl;

wherein $R_1$ is heteroalkyl, comprising an oxygen heteroatom;

wherein $R_1$ is methyl-diethylene glycol (—CH2OCH2CH2OCH2CH3);

wherein $R_2$ is H or optionally substituted, lower (C1-C5) alkyl;

wherein $R_2$ is methyl, ethyl, propyl or butyl;

wherein $R_3$ is H or optionally substituted, lower (C1-C5) alkyl;

wherein $R_3$ is H, methyl, ethyl, propyl or butyl;

wherein $R_4$ is methoxy;

wherein R₄ has the structure 2:

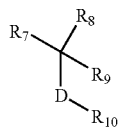

wherein R₇ is selected from a bond, optionally substituted lower alkyl, NH, S and O; R₈ and R₉ are independently selected from hydrogen and optionally hetero-, optionally substituted alkyl; and D is selected from C, N, and R₁₀ is a 5-7 membered, optionally heterocyclic ring, particularly wherein R₈ is H and R₉ is methylmethoxy (—CH₂OCH₃);
wherein R₅ is R₆(CH₂)$_n$ wherein R₆ is a 5-7 membered, optionally heterocyclic ring, and n is an integer from 0 to 5;
wherein R₅ is benzyl;
wherein A is CH₂, O, S, NH or N—(C1-C3) alkyl;
wherein G is O, S, NH or N—(C1-C3) alkyl;
wherein X is hydroxyl, amino, (C1-C4) alkylamino, or (C1-C4) alkylthio;
wherein Y is C, N, O or S (wherein the X—Y bond encompasses both diastereomers);
wherein Z is CH₂, O, S, NH or N—(C1-C3) alkyl;
wherein the inhibitor is selected from structures set forth herein, particularly BK1114, BK1165, PH1152 and the compounds of Table 1.

The subject compositions may be co-formulated or coadministered or coprescribed with an additional active ingredient such as (i) an appetite-suppressant or antiobesity drug such as Orlistat, Sibutramine, Metformin, Byetta, Symlin, and Rimonabant; (ii) an anti-diabetic drug such as (a) Insulin; (b) Secretagogues including Sulfonylureas such as glipizide (Glucotrol), glyburide (Diabeta, Micronase, Glynase), glimepiride (Amaryl), gliclazide (Diamicron) and Meglitinides, such as repaglinide (Prandin) and nateglinide (Starlix) (c) Sensitizers including Biguanides such as metformin and Thiazolidinediones such as rosiglitazone and pioglitazone; (d) Alpha-glucosidase inhibitors such as miglitol (Glyset) and acarbose (Precose/Glucobay); and (e) Peptide analogs including Incretin mimetics, Glucagon-like peptide (GLP) analogs and agonists such as Exenatide and Liraglutide, Gastric inhibitory peptide (GIP) analogs, DPP-4 inhibitors such as vildagliptin and sitagliptin, and Amylin analogues; or (iii) a cholesterol-modulating drug such as HMG-CoA reductase inhibitors.

The invention also encompasses methods of formulating, using the subject compounds and compositions, including methods of inhibiting GOAT, comprising the step of contacting the GOAT with a subject compound or composition, and optionally, detecting a resultant inhibition of the GOAT. The target GOAT is usually endogenous, in vivo, in a patient determined to be in need of GOAT inhibition, such as patients determined or diagnosed to be suffering from obesity, diabetes, hypercholesterolemia, etc.

DESCRIPTION OF PARTICULAR
EMBODIMENTS OF THE INVENTION

The following descriptions are provided by way of illustration only and not by way of limitation. Those skilled in the art will readily recognize a variety of noncritical parameters that could be changed or modified to yield essentially similar results.

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

As used herein, the term "heteroatom" is meant to include oxygen (O), nitrogen (N), sulfur (S) and silicon (Si).

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH2-CH2-CH2-CH2-. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH2-CH2-O—CH3, —CH2-CH2-NH—CH3, —CH2-CH2-N(CH3)-CH3, —CH2-S—CH2-CH3, —CH2-CH2, —S(O)—CH3, —CH2-CH2-S(O)2-CH3, —CH=CH—O—CH3, —Si(CH3)3, —CH2-CH=N—OCH3, and —CH=CH—N(CH3)-CH3. Up to two heteroatoms may be consecutive, such as, for example, —CH2-NH—OCH3 and —CH2-O—Si(CH3)3.

Similarly, the term "heteroalkylene," by itself or as part of another substituent means a divalent radical derived from heteroalkyl, as exemplified by —CH2-CH2-S—CH2-CH2- and —CH2-S—CH2-CH2-NH—CH2-. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2 m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2 m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term "heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO2R', —CONR'R", —OC(O)NR'R", —NR"C(O)R', —NR'—C(O)NR"R'", —NR'—SO2NR'", —NR"CO2R', —NH—C(NH2)=NH, —NR'C(NH2)=NH, —NH—C(NH2)=NR', —S(O)R', —SO2R', —SO2NR'R", —NR"SO2R, —CN and —NO2, in a number ranging from zero to three, with those groups having zero, one or two substituents being particularly preferred. R', R" and R'" each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF3 and —CH2CF3).

Preferred substituents for the alkyl and heteroalkyl radicals are selected from: —OR', =O, —NR'R", —SR', halogen, —SiR'R"R'", —OC(O)R', —C(O)R', —CO2R', —CONR'R", —OC(O)NR'R", —NR"C(O)R', —NR"CO2R', —NR'—SO2NR"R'", —S(O)R', —SO2R', —SO2NR'R", —NR"SO2R, —CN and —NO2, where R' and R" are as defined above. Further preferred substituents are selected from: —OR', =O, —NR'R", halogen, —OC(O)R', —CO2R', —CONR'R", —OC(O)NR'R", —NR"C(O)R', —NR"CO2R', —NR'—SO2NR"R'", —SO2R', —SO2NR'R", —NR"SO2R, —CN and —NO2.

Similarly, substituents for the aryl and heteroaryl groups are varied and selected from: halogen, —OR', —OC(O)R', —NR'R", —SR', —R', —CN, —NO2, —CO2R', —CONR'R", —C(O)R', —OC(O)NR'R", —NR"C(O)R', —NR"CO2R', —NR'—C(O)NR"R'", —NR'—SO2NR"R'", —NH—C(NH2)=NH, —NR'C(NH2)=NH, —NH—C (NH2)=NR', —S(O)R', —SO2R', —SO2NR'R", —NR"SO2R, —N3, —CH(Ph)$_2$, perfluoro(C1-C4)alko-xy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO2, —CO2R', —CONR'R", —C(O)R', —OC(O)NR'R", —NR"C(O)R', —S(O)R', —SO2R', —SO2NR'R", —NR"SO2R, —N3, —CH(Ph)2, perfluoro (C1-C4)alkoxy and perfluoro(C1-C4)alkyl, where R' and R" are as defined above. Further preferred substituents are selected from: halogen, —OR', —OC(O)R', —NR'R", —R', —CN, —NO2, —CO2R', —CONR'R", —NR"C(O)R', —SO2R', —SO2NR'R", —NR"SO2R, perfluoro(C1-C4) alkoxy and perfluoro(C1-C4)alkyl.

The substituent —CO2H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH2)$_q$-U—, wherein T and U are independently —NH—, —O—, —CH2- or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH2-, —O—, —NH—, —S—, —S(O)—, —S(O)2-, —S(O) 2NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH2)s-X—(CH2)t-, where s and t are independently integers of from 0 to 3, and X is —O—, —NR'—, —S—, —S(O)—, —S(O)2-, or —S(O)$_2$NR'—. The substituent R' in —NR'— and —S(O)2NR'— is selected from hydrogen or unsubstituted (C1-C6)alkyl.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen-carbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, diastereomers, geometric isomers and individual isomers are all intended to be encompassed within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat a disease associated with undesirably high GOAT activity, particularly as found in obesity.

Accordingly, the invention provides methods of treating a disease associated with undesirable GOAT activity, the method comprising the step of administering an effective dosage of the subject compounds and compositions, which may be followed by the step of detecting a resultant decrease in pathology associated with the disease, and which may be prefaced by the step of diagnosis such disease and/or prescribing such composition. Applicable disease include obesity, diabetes and hypercholesterolemia.

The invention also provides methods of inhibiting a GOAT, the method comprising the step of contacting a composition comprising a GOAT with an effective amount of the subject compounds and compositions, which may be followed by the step of detecting a resultant change in GOAT activity.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the inhibitor is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the inhibitors may be advantageously used in conjunction with other therapeutic agents as described herein or otherwise known in the art. Hence the compositions may be administered separately, jointly, or combined in a single dosage unit.

The amount administered depends on the inhibitor formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The following are examples (Formulations 1-4) of inhibitor capsule formulations.

TABLE 1

Capsule Formulations

| | Capsule Formulation | | | |
|---|---|---|---|---|
| | Formula 1 mg/capsule | Formula 2 mg/capsule | Formula 3 mg/capsule | Formula 4 mg/capsule |
| Inhibitor (Solid Solution) | 100 | 400 | 400 | 200 |
| Silicon Dioxide | 0.625 | 2.5 | 3.75 | 1.875 |
| Magnesium Stearate NF2 | 0.125 | 0.5 | 0.125 | 0.625 |
| Croscarmellose Sodium NF | 11.000 | 44.0 | 40.0 | 20.0 |
| Pluronic F68 NF | 6.250 | 25.0 | 50.0 | 25.0 |
| Silicon Dioxide NF | 0.625 | 2.5 | 3.75 | 1.875 |
| Magnesium Stearate NF | 0.125 | 0.5 | 1.25 | 0.625 |
| Total | 118.750 | 475.00 | 475.00 | 475.00 |
| Capsule Size | No. 4 | No. 0 | No. 0 | No. 2 |

Preparation of Solid Solution

Crystalline inhibitor (80 g/batch) and the povidone (NF K29/32 at 160 g/batch) are dissolved in methylene chloride (5000 mL). The solution is dried using a suitable solvent spray dryer and the residue reduced to fine particles by grinding. The powder is then passed through a 30 mesh screen and confirmed to be amorphous by x-ray analysis.

The solid solution, silicon dioxide and magnesium stearate are mixed in a suitable mixer for 10 minutes. The mixture is compacted using a suitable roller compactor and milled using a suitable mill fitted with 30 mesh screen. Croscarmellose sodium, Pluronic F68 and silicon dioxide are added to the milled mixture and mixed further for 10 minutes. A premix is made with magnesium stearate and equal portions of the mixture. The premix is added to the remainder of the mixture, mixed for 5 minutes and the mixture encapsulated in hard shell gelatin capsule shells.

The inhibitors can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent inhibitors, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as inhibitor potency, severity of the disease being treated. For example, a dosage regimen of the inhibitors can be oral administration of from 10 mg to 2000 mg/day, preferably 10 to 1000 mg/day, more preferably 50 to 600 mg/day, in two to four (preferably two) divided doses. Intermittant therapy (e.g., one week out of three weeks or three out of four weeks) may also be used.

In Vitro Octanoylation Assay Details.

The assay we used is described in copending U.S. Ser No. 12/167,917, filed: Jul. 3, 2008. For baculoviral infection of insect cells, mouse GOAT cDNA was inserted into pFastBac HT-A (His10-tag) (Invitrogen), and baculovirus was generated. Sf9 insect cells were cultured, set up on day 0 at a density of $5 \times 10^5$ cells/ml, and infected on day 1 with baculovirus encoding His 10-GOAT at a density of $1 \times 10^6$ cells/ml. Cells were harvested 48 h post-infection and washed once with phosphate-buffered saline.

Each pellet of Sf9 cells (obtained from 1 liter of cell culture) was disrupted with a Dounce homogenizer (40 strokes) on ice in 50 ml of buffer containing 50 mM Tris-Cl (pH 7.0), 150 mM NaCl, 1 mM sodium EDTA, 1 mM dithiothreitol, 100 µM bis(4-nitrophenyl) phosphate, 2.5 µg/ml aprotinin, 20 µg/ml phenylmethylsulfonyl fluoride, 10 µg/ml leupeptin, and 10 µg/ml pepstatin A. After an initial centrifugation at 3,000 g for 5 min at 4° C., the supernatant was further centrifuged at 100,000 g for 30 min at 4° C. to obtain a membrane fraction, which was stored at −80° C. until the time of assay. Just prior to assay, the membranes were suspended in 50 mM HEPES-NaOH (pH 7.0) and then passed through a 22-gauge needle 10 times. After centrifugation at 1,000 g for 1 min to remove aggregated materials, the supernatant (hereafter referred as membranes) was used for assays.

Unless otherwise stated, the standard assay mixture contained 50 mM HEPES-NaOH (pH 7.0), 50 µM palmitoyl CoA or myristyl ether CoA, 50 µg membrane protein, 5 µg recombinant wild type or mutant versions of proghrelin-His8 and 1 µM [$^3$H]octanoyl CoA (11 dpm/fmol) in a final volume of 50 µl. After incubation at 37° C. for 5 min, each reaction was stopped by the addition of 1 ml of buffer A (50 mM Tris-Cl at pH 7.5, 150 mM NaCl, and 0.1% (w/v) SDS), after which each sample was loaded onto a 0.2-ml nickel-affinity column (QIAGEN). The columns were washed at room temperature with 1 ml of buffer A followed by 3 ml of buffer A containing 25 mM imidazole. The His-tagged proghrelin was then eluted with 1 ml of buffer A containing 250 mM imidazole. Radioactivity present in the 250 mM-imidazole eluate was quantified by liquid scintillation counting.

Design and Synthesis of Small Molecule GOAT Inhibitors

While details of the GOAT catalyzed acylation are not yet clear, biochemical data is consistent with an intermediate of type 1A being generated at some point along the reaction coordinate. In this mechanism, the serine-3 hydroxyl group of GOAT bound ghrelin would be deprotonated by an active site base (e.g. histidine). The resultant alkoxide would add to the carbonyl carbon of either an acylated enzyme residue or to the thioester of separately bound octanoylCoA. Species 1A thus formed would presumably resemble the transition state for the reaction. Enzymes are thought to enhance reaction rates (forward and back) by lowering the energy required to reach the transition state (TS) of the processes they catalyze. This is achieved, in part, by the TS geometry being bound favorably. Tight binding but non-reactive mimics of TS geometries spawned the field of catalytic antibodies as originally envisioned by Pauling, and they have also become useful as specific enzyme inhibitors.

In the GOAT forward reaction, we reasoned that 1A would collapse to release R— and ester product. The enzyme is selective for transferring an eight-carbon fatty acid, and conserved ghrelin residues flanking serine-3 are required for efficient catalysis. We combined these elements into a single design. Namely, we would synthesize compounds able to bind GOAT in a manner similar to the tetrahedral oxyanion in 1A—and where the tetrahedral geometry at that site would be stable (1B). The molecules would further possess a hydrophobic segment of appropriate size to exploit GOAT selectivity for octanoylation. Lastly, the molecules would contain sufficient additional functionality to occupy part of the (pro) ghrelin binding space—wherein favorable interactions such as hydrogen-bonding could further stabilize binding and slow the dissociation rate of an enzyme/inhibitor complex.

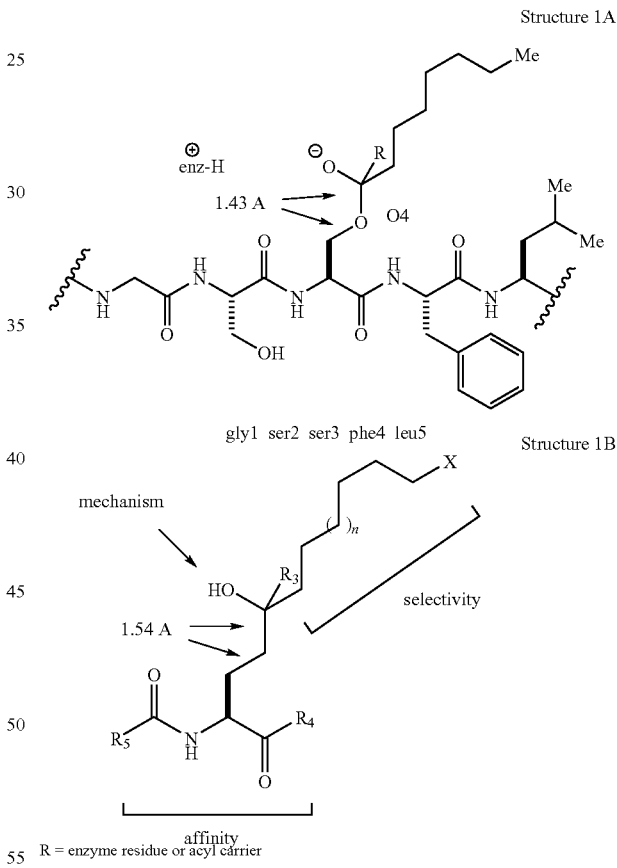

Replacing O4 in 1A with carbon while choosing R3 (1B) to be a poor leaving group was considered a means to access transition state mimetics for the acyl transfer. We targeted an (S)-2-amino-5-hydroxy lauric acid core (1B) that could be elaborated as needed. There was no literature describing syntheses of such compounds and therefore a de novo preparation was developed.

We transformed commercial L-methionine methyl ester hydrochloride into (S)—N—Z-vinylglycine (2) using Rapoport's protocols (Scheme 1) and subsequently cross metathesized this material with racemic 1-decene-3-ol (3) using Grubbs' ruthenium alkylidene A as catalyst. The resultant composite product (PH1147) was then hydrogenolyzed in MeOH to afford amino alcohol PH1148. This material was condensed independently with 3-hydroxy-3-methylbutyric acid and 2,2-dimethyl-3-hydroxy propionic acid to give PH1149 and PH1150, respectively. The latter was saponified in aqueous LiOH and the derived acid condensed with commercial (S)-(+)-α-(methoxymethyl)phenethylamine (B) to afford PH1152.

Scheme 1

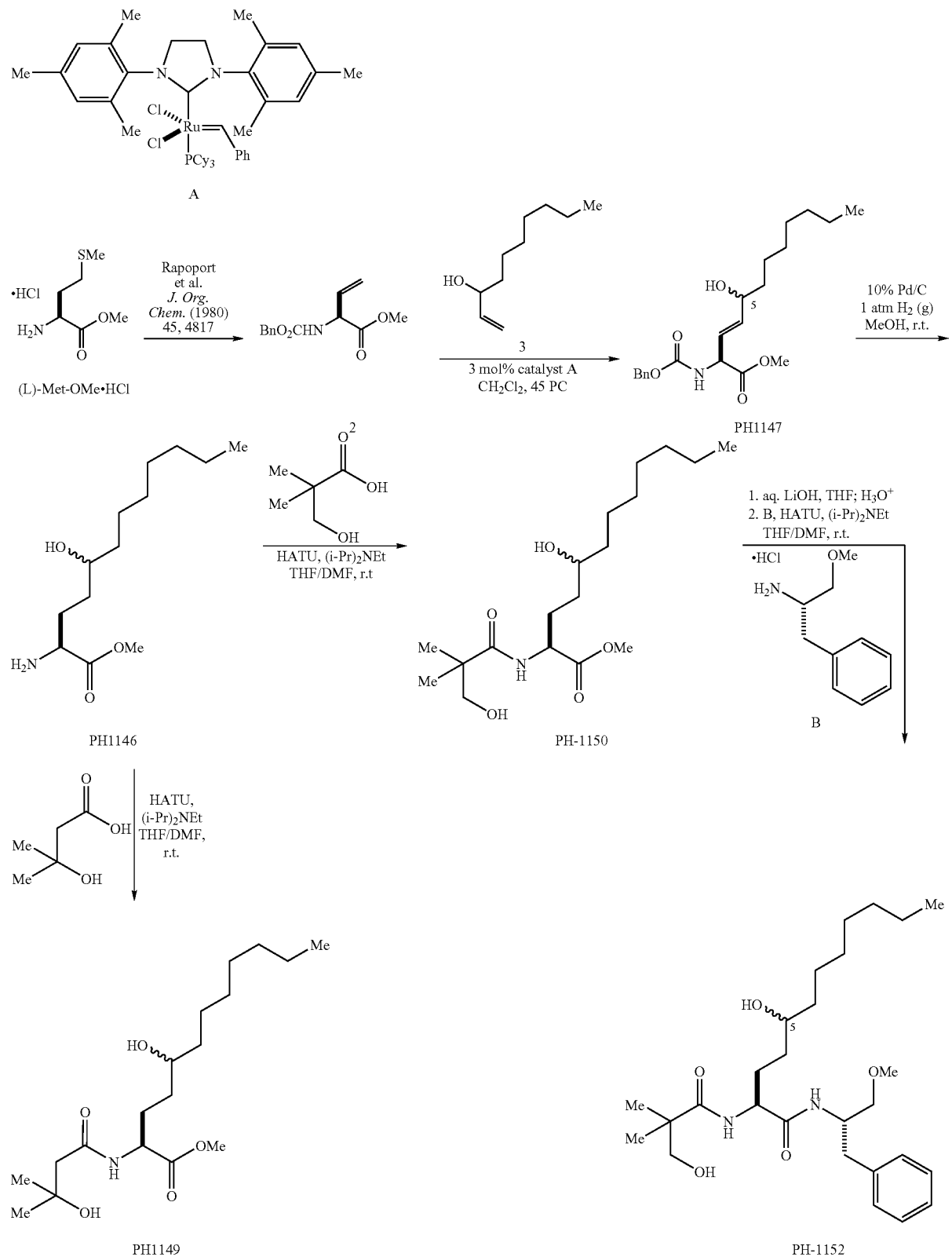

This completed our initial set of potential GOAT inhibitors. Each compound was isolated as an ~1:1 mixture of C5 epimers (the result of using racemic decenol in the metathesis with optically active 2). The epimers were not separated because, if the intended mode of inhibition were to operate, wherein the inhibitor's secondary alcohol would mimic the tetrahedral oxyanion in 1, the GOAT active site would presumably accommodate one C5 diastereomer better than the other, yet there was no way to predict which one at this stage Compounds PH1147-1152 were screened for GOAT inhibition in vitro using membrane fractions prepared from Sf9 insect cells infected with baculovirus encoding mouse GOAT. The assay (described in U.S. Ser. No. 12/167,917) measures the extent of specific acyl transfer from tritiated octanoylCoA to recombinant His-tagged proghrelin. PH1147, PH1149, PH1150 and PH1152 inhibited GOAT activity at a high concentration (500 μM) with PH1147 and PH1152 showing the greatest inhibition, and when titrated to lower concentrations, PH1147 performed best ($IC_{50}$~90 μM). PH1147 was the simplest molecule in the set and lacked motifs present in the more complex analogs intended to be Ser2 and/or Phe4 mimetics.

To probe the series further, we hydrogenated PH1147 in the presence of catalytic amounts of Crabtree's iridium complex C (Scheme 2). Unlike the hydrogenolysis of PH1148 wherein both the olefin and the benzyloxycarbonyl groups were reduced, this alcohol-directed reduction using C selectively saturates the alkene to afford PH1154. Competing isomerization of the alkene to an enol in situ was also observed and PH1154 was produced alongside ketone PH1154a. Fortunately the two were readily separable by silica gel chromatography. With PH1154 in hand, the material was saponified with aqueous LiOH and the incipient acid condensed with (S)-(+)-α-(methoxymethyl)phenethylamine (B) to afford PH1156. Both PH1154a and PH1156 inhibit GOAT comparably to PH1147 at 100 μM concentrations in vitro; however, they performed more poorly at higher concentrations.

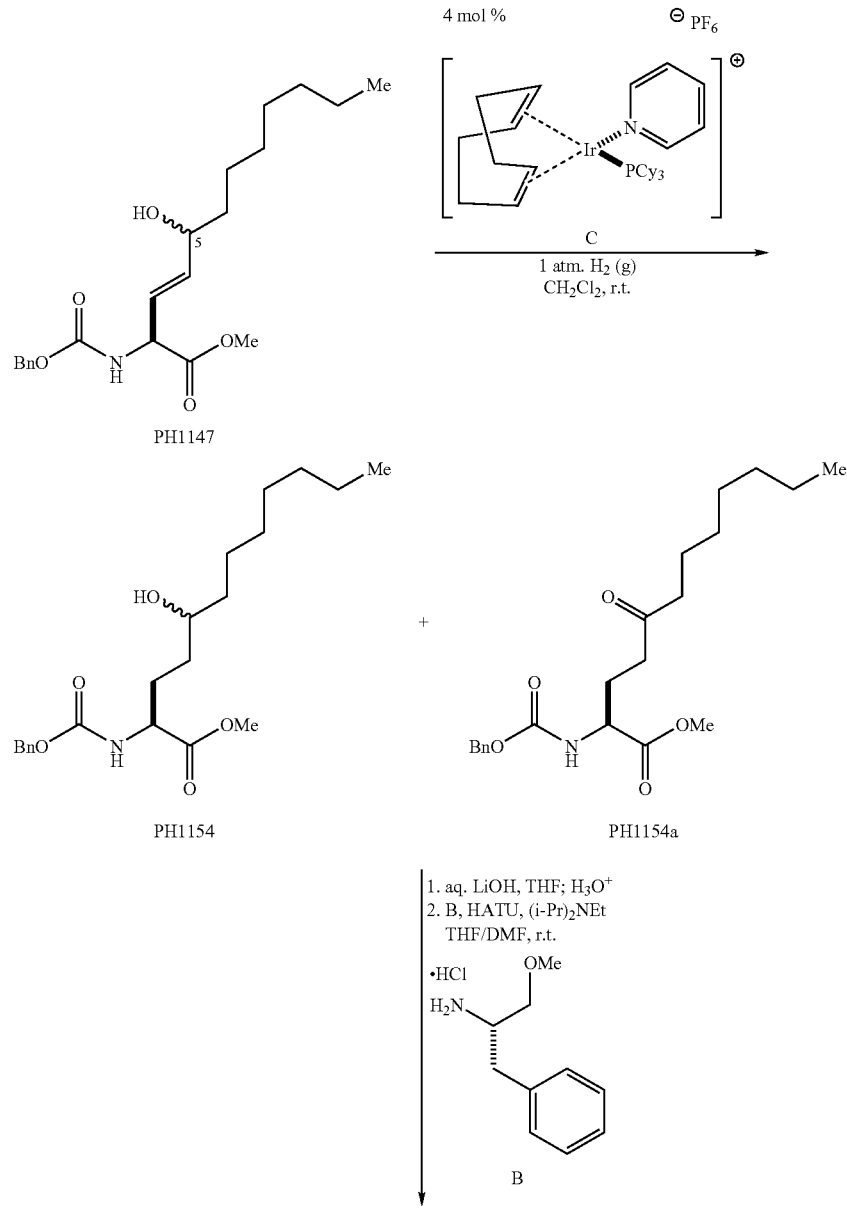

Scheme 2

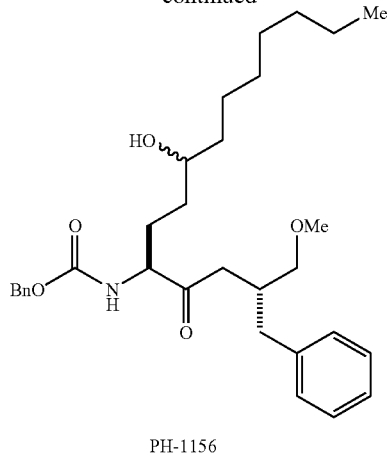

PH-1156

It appeared perhaps the benzoxylcarbonyl (a.k.a. Z) protecting group in PH1147 was actually a beneficial feature. We noted also that PH1147 was the one compound in the series retaining the trans alkene from the metathesis reaction. To explore these issues, we removed the Z group from PH1156 to afford PH1159 and reduced the ester of PH1147 to provide diol PH1165. The latter was elaborated to PH1167 wherein an N-methylglycine-alanine dipeptide was installed as a potential surrogate for gly1 and ser2 of ghrelin. However, neither PH1159 nor PH1167 possessed activity comparable to PH1147 while PH1165 was only slightly less active. These observations supported the idea that the Z group contributed positively to inhibition. Adding segments of ghrelin peptide in place of the Z group was not helpful nor was replacing it with a trifluoroacetyl unit (see BK1112). Still, PH1147 activity was weak and we needed an indication that inhibition was consistent with known GOAT preferences.

Along these lines we synthesized BK1114 by cross metathesizing vinyl glycine 2 with racemic 3-hydroxy-3-methyl-1-decene (4), itself prepared by homologating 2-nonanone with dimethylsulfonium methylide (Scheme 3). BK1114 is identical to PH1147 except that the C5 hydrogen atom is replaced with a methyl group. This substitution allowed us to begin probing tolerance in the C5 region, which corresponds to 'R' in 1 and would be either the sulfur of CoA Scheme 3

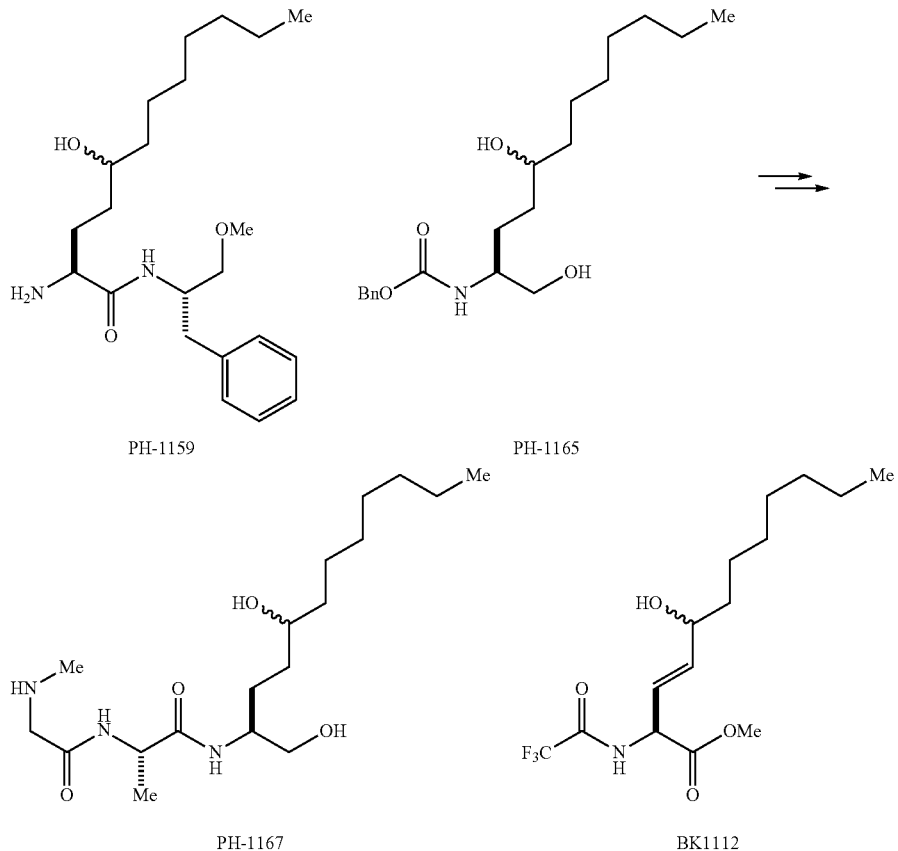

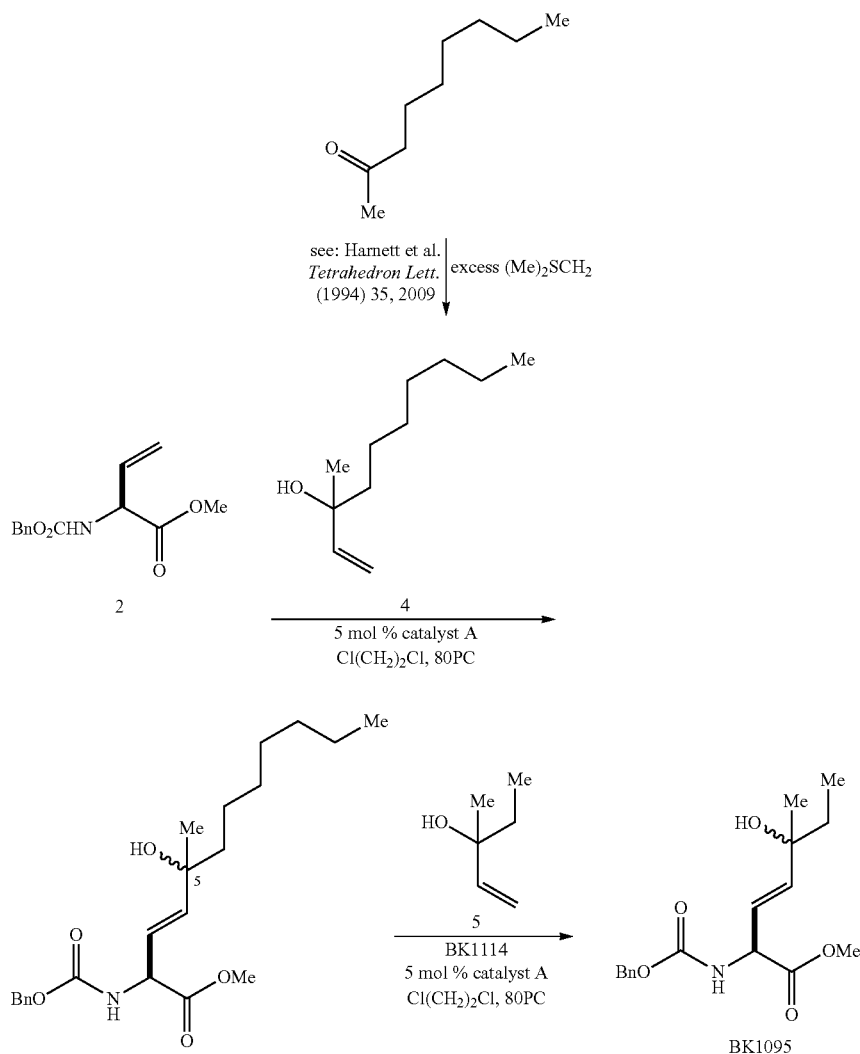

or a non-hydrogen atom from a GOAT active site residue. BK1114 is roughly twice as efficacious as PH1147 in inhibiting GOAT in vitro at 100 μm concentration. Furthermore, beginning with 2 and 3-hydroxy-methyl-1-pentene (5) we synthesized BK1095. This molecule is identical to BK1114 except its hydrocarbon chain is truncated by five atoms. BK1095 shows little inhibition of GOAT activity at all concentrations tested—suggesting the system is responding to hydrocarbon chain length consistent with GOAT selectivity for octanoylation.

During this time it was discovered that GOAT activity was subject to end-product inhibition and that replacing the ester linkage in octanoylated ghrelin (1-28) with the corresponding amide improved performance significantly. This same trend held with octanylated ghrelin pentapeptides. The first five N-terminal residues having serine-3 replaced by (S)-2,3-di-aminopropionic acid and the distal amine of this unit octanoylated (Structure 2) was an inhibitor showing an $IC_{50}$ of ~1.5 μM in vitro. It was essential to cap the C-terminus as a primary carboxamide in this case. We decided to examine similar C-terminal extensions in our series.

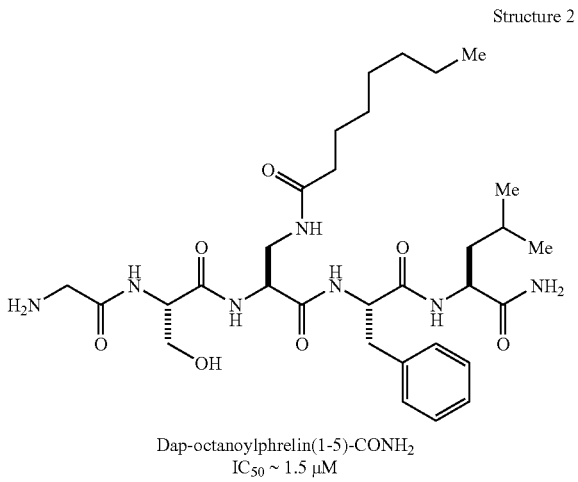

Structure 2

Dap-octanoylphrelin(1-5)-CONH$_2$
$IC_{50}$ ~ 1.5 μM

We saponified BK1114 with aqueous LiOH and condensed the resultant acid with commercial Phe-Leu-CONH$_2$ hydrochloride to afford BK1129 (Scheme 4). It was possible to separate the C5 diastereomers of this material by preparative HPLC. The two isomers were assayed independently for GOAT inhibition. Neither was as effective as BK1114 in terms of potency. We hypothesized that the Z group in BK1114 was binding to GOAT such that its phenyl group occupied a binding pocket reserved for Phe4 of ghrelin (Scheme 5). Such binding would presumably require rotation about Cα-Cβ bond in BK1114 wherein S stereochemistry at Cα would actually appear unnatural to the enzyme. Moreover, it would orient functionality slated to occupy ghrelin Phe5 and Leu5 space in the opposite direction. We tested this idea by synthesizing BK1149. This molecule is derived from D-methionine and is epimeric at Cα relative to BK1114. We also synthesized BK1135 wherein the methyl ester was removed entirely.

BK1149 retains activity in vitro comparable to BK1114 while BK1135 is less potent. We also synthesized BK1137 and BK1141 wherein the Z group was replaced with the β-hydroxy-α,α'-dimethylpropionamide unit first used in PH1152 (see Scheme 1).

Scheme 4

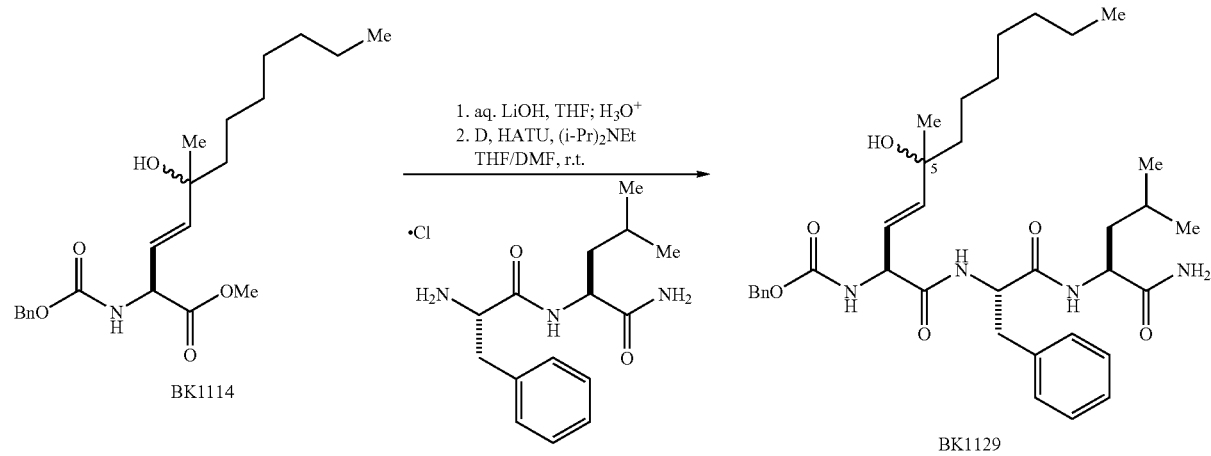

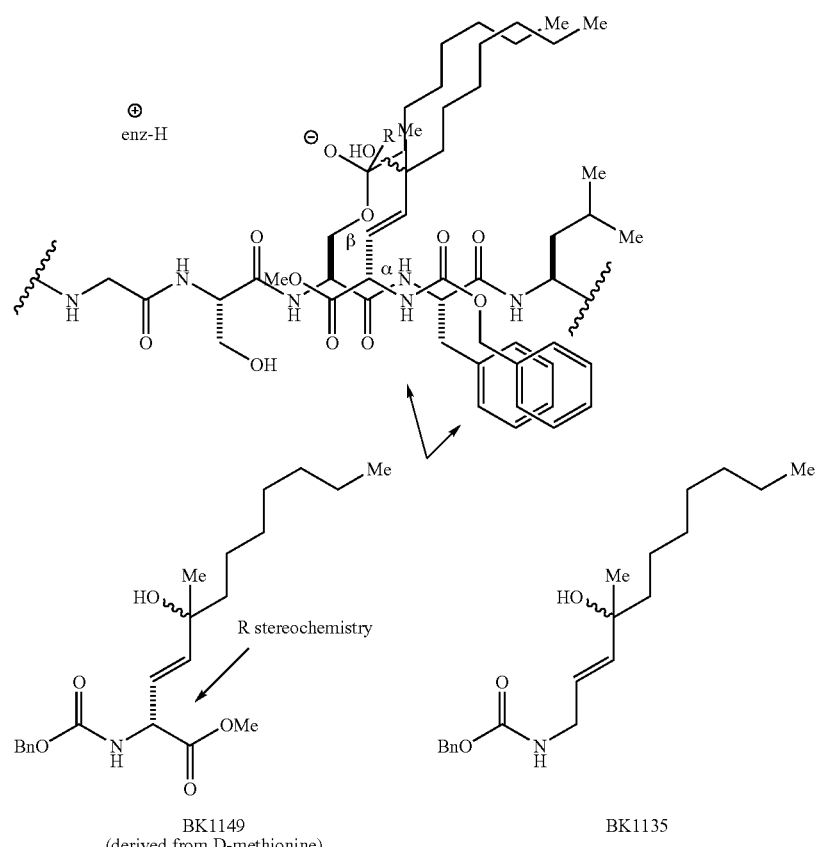

Hypothetical binding mode for the group in PH1147/BK1114 (overlay with putative GOAT transition state 1) to explain why C-terminal peptidyl extensions may be detrimental Note: orienting the phenyl group of BK1114 (black) into a ghrelin Phe4 binding pocket preumable would require rotation about Cα-Cβ bond such that the S stereochemistry as Cα would actually appear unnatural to the enzyme.

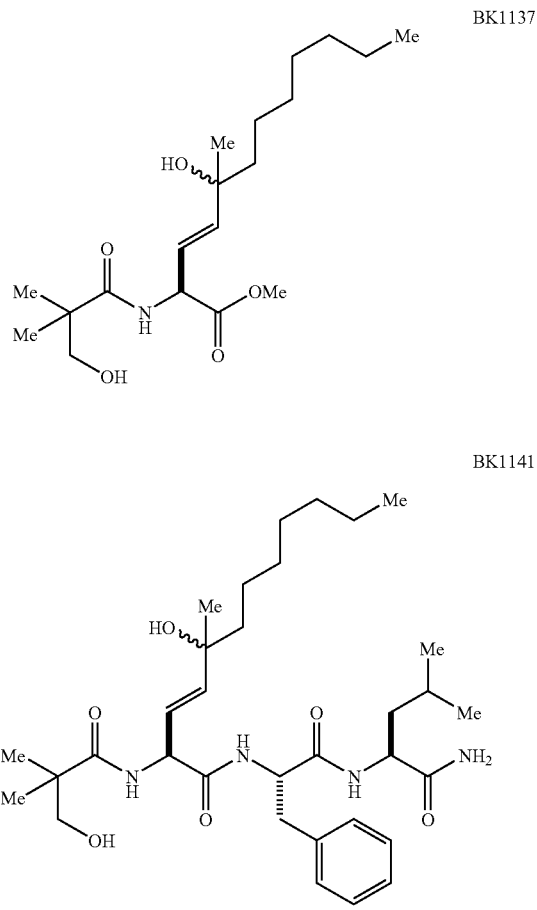

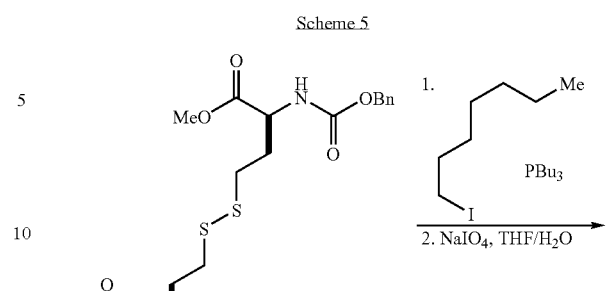

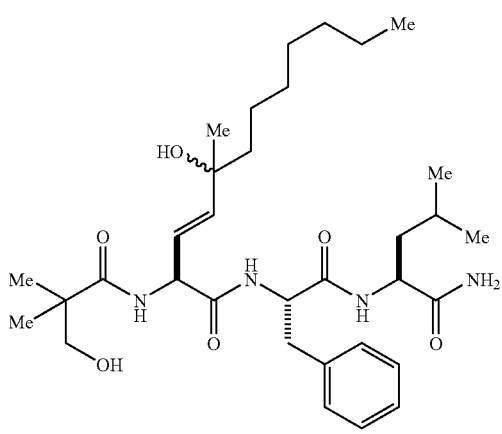

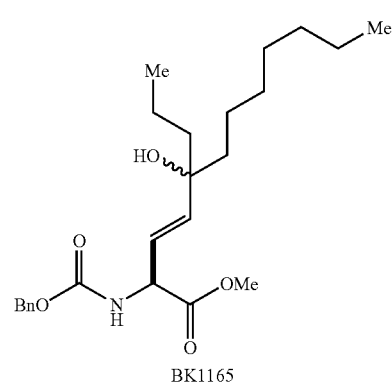

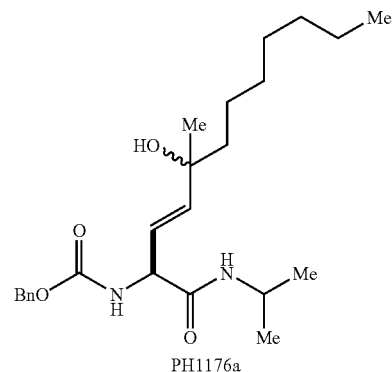

BK1141 has a phenylalanine unit and retains some activity however BK1137, which lacks both the Z group and a phenylalanine residue, is essentially inactive. Taken together, the data our postulated binding mode for BK1114 and suggest in such an orientation the stereochemistry at Cα is not specifically recognized by the enzyme (i.e. BK1114 and BK1149 are similarly efficacious).

We have used an alcohol group as a mimic of the tetrahedral oxyanion in the putative transition state for acyl transfer. Alternative functional groups can potentially fill this role; for example, the known homocysteine dimer 6 was reductively alkylated with iodooctane in the presence of tributylphosphine (Scheme 5). The resultant S-octylhomocysteine derivative was oxidized to the corresponding sulfoxide BK1145 with sodium periodate. Dialkyl sulfoxides maintain a tetrahedral geometry and are chiral at sulfur. BK1145 was isolated as a mixture of diastereomers. While not as potent as BK1114, the molecule does inhibit GOAT in a dose responsive manner.

We also examined octanoylated (S)-2,3-diaminopropionic ester LN1111622 as a simplified version of DapOctanoylghrelin(1-5)CONH$_2$. This molecule would presumably not function as a transition state inhibitor but rather be a surrogate for the product of GOAT activity. The compound does not perform as well as BK1114.

-continued

PH1176b

In summary, ispropylamide analogs of BK1114 (namely PH1176a & PH1176b) do not improve activity; however, the C5 methyl group can be replaced with propyl without compromising activity (see BK1165).

Inhibition of GOAT Activity by BK1114 in Intact Cells.

A stably transfected INS-1 cell line co-expressing pre-proghrelin and GOAT was established as described below. On day 0, cells were set up at a density of $1.5 \times 10^6/100$-mm dish in medium A (RPMI-1640 medium supplemented with 10 mM HEPES, 50 μM β-mercaptoethanol, 100 U/ml penicillin, and 100 μg/ml streptomycin) containing 10% (v/v) FCS. On day 2, fresh medium was added. On day 4, the cells received a direct addition of the indicated concentration of BK1114 delivered in DMSO. The final concentration of DMSO in each dish was 0.5%. 24 h after treatment, two dishes of cells from each condition were harvested and pooled, after which peptides were extracted from the cells, fractioned on reverse-phase chromatography, and subjected to immunoblot analysis with a 1:1000 dilution of rabbit anti-ghrelin antibody as previously described (Yang J, Brown M S, Liang G, Grishin N V, Goldstein J L (2008) Identification of the acyltransferase that octanoylates ghrelin, an appetite-stimulating peptide hormone. Cell 132:387-39). Films were exposed for 1 min.

Stably transfected cell line co-expressing preproghrelin and GOAT. Rat INS-1 cells were grown in monolayer at 37° C. in 8.8% $CO_2$ as previously described (Id.). On day 0, cells were plated at a density of $5 \times 10^5/100$-mm dish in medium A (see above) containing 10% (v/v) FCS. On day 1, cells were transfected with 5 μg of pCMV-preproghrelin using FuGENE HD Transfection Reagent (Roche) according to the manufacture's instructions. 24 h after transfection, the cells were switched to medium A containing 10% FCS and 400 μg/ml G418 to select the cells expressing the neo-containing pCMV-preproghrelin plasmid. Fresh medium was added every 2 to 3 days until colonies formed at ~14 days. Individual colonies were isolated with cloning cylinders and then subcloned by dilution plating. Expression of proghrelin and ghrelin was assessed by immunoblot analysis. After the establishment of the cell line expressing preproghrelin, the preproghrelin-expressing cells were set up on day 0 at a density of $5 \times 10^5/100$-mm dish in medium A containing 10% (v/v) FCS. On day 1, cells were transfected with 3 μg of pEF-GOAT-T7 using FuGENE HD Transfection Reagent (Roche) according to the manufacture's instructions. 24 h after transfection, the cells were switched to medium A containing 10% FCS and 0.2 μg/ml puromycin to select the cells expressing the pac-containing pEF-GOAT-T7 plasmid. Subcloning of the cell line was the same as mentioned above. Expression of GOAT-T7 was assessed by immunoblot analysis. The results of these experiments demonstrated a BK1114 dose inhibition response from 5 to 10 to 20 to 50 uM inhibitor.

Inhibition of GOAT activity by [$Dap^3$]octanoyl-ghrelin (1-5)-NH2 peptide and BK1114. Membranes from Sf9 cells infected with baculovirus encoding mouse $His_{10}$-GOAT were prepared as previously described (Yang J, Zhao T J, Goldstein J L, Brown M S. 2008 PNAS, 105: 10750-10755). Each 50-μl reaction mixture contained 50 μg of membrane protein, 5 μg of proghrelin-$His_8$, 50 μM palmitoyl CoA, 1 μM http[$^3$H] octanoyl CoA (11 dpm/fmol), and the experimental concentrations of peptide or compound in a final concentration of 3% (vol/vol) DMSO. Control values were established which represent the amount of [3H]octanoyl proghrelin formed in the absence of compound. The results of demonstrated dose response inhibition by both the pentapeptide and by BK1114.

Inhibition of GOAT activity by the synthetic compounds, BK1114, BK1176, BK1177 and BK1183. Membranes from Sf9 cells infected with baculovirus encoding mouse $His_{10}$-GOAT were prepared as previously described (Yang et al., 2008, supra). Each 50-μl reaction mixture contained 50 μg of membrane protein, 5 μg of proghrelin-$His_8$, 50 μM palmitoyl CoA, 1 μM [$^3$H]octanoyl CoA (11 dpm/fmol), and the experimental concentrations of the compound in a final concentration of 3% (vol/vol) DMSO. Control values were established which represent the amount of [3H]octanoyl proghrelin formed in the absence of compound. The results demonstrated dose response inhibition by each of the test compounds.

Organic Synthesis

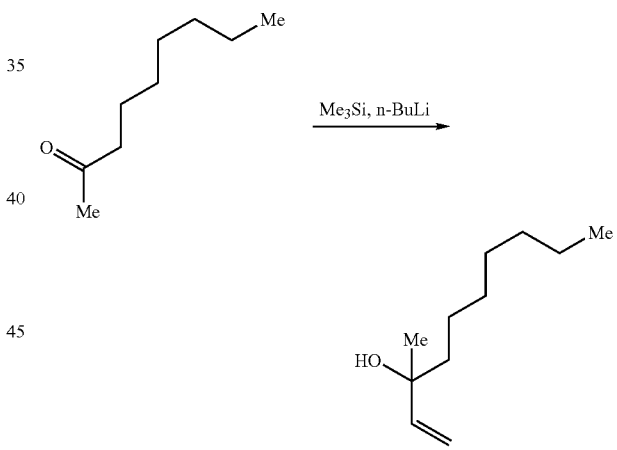

BK1114. Trimethylsulfonium iodide (23.53 g, 115.3 mmol) was suspended in anhydrous THF (250 mL) under argon and the slurry cooled to −20° C. A pre-cooled (−20° C.) solution of n-BuLi (2.14M in hexanes, 51.2 mL, 109 mmol) was added slowly via cannulating needle and the solution stirred for 10 minutes at −20° C. A pre-cooled (−20° C.) solution 2-nonanone (5.0 mL, 28.8 mmol) was then added slowly via cannulating needle and the resultant solution was stirred at −20° C. for 1 hour. The reaction was allowed to warm to room temperature over 2 hours. Water (200 mL) was added and the mixture was extracted with $Et_2O$ (3×100 mL). The combined organics were dried over MgSO4, filtered and concentrated in vacuo to afford an oily residue. This material was chromatographed on silica gel (eluting with 10% EtOAc/hexanes) to afford 3-hydroxy-3-methyl-1-decene (3.56 g, 72% yield) as a colorless oil.

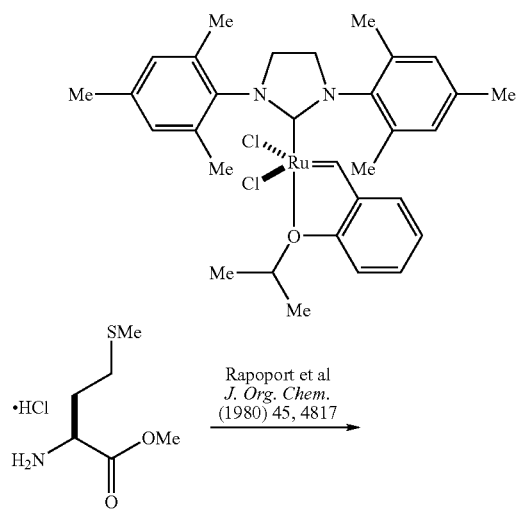

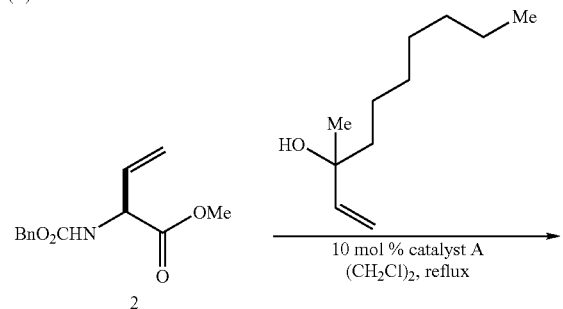

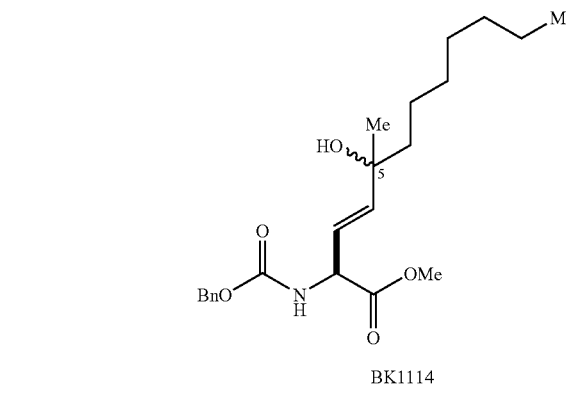

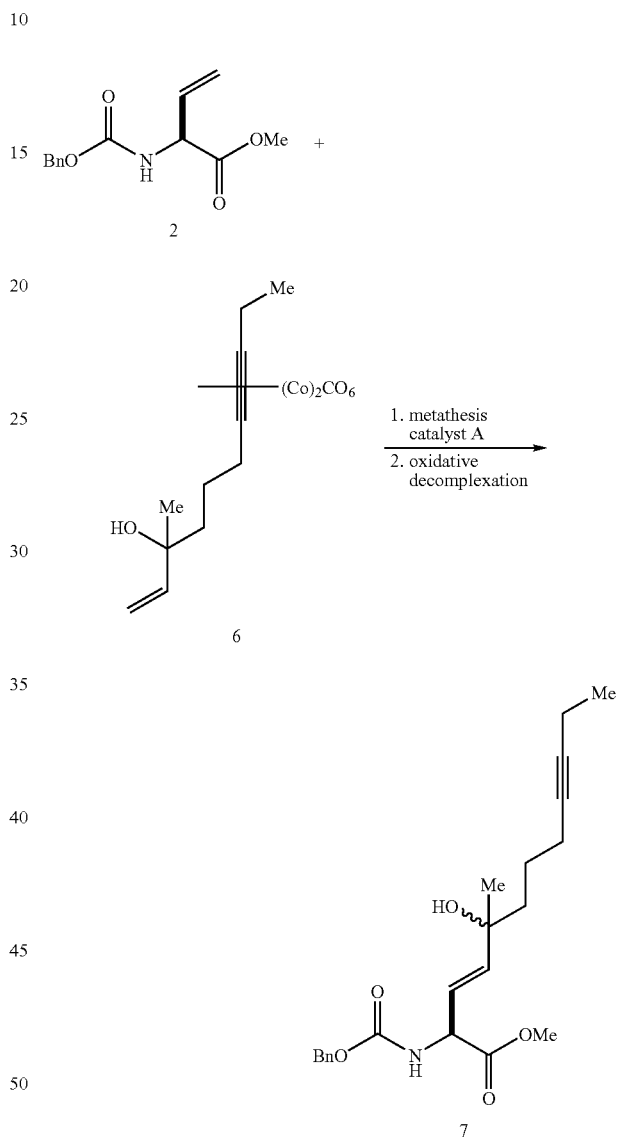

N—Z—(S)-vinylglycine (2) was prepared from L-methionine as described previously [Rapoport et al. *J. Org. Chem.* (1980) 45, 4817].

N—Z—(S)-vinylglycine (2: 55 mg, 0.22 mmol) and 3-hydroxy-3-methyl-1-decene (74 mg, 0.44 mmol) were each dissolved in 0.3 mL anhydrous 1,2-dichloroethane. The two solutions were added separately, and simultaneously, dropwise by syringe to a solution of ruthenium complex A (Aldrich Chemical Co., 13.7 mg, 0.021 mmol) in 0.5 mL 1,2-dichlorethane under an argon atmosphere. When the additions were complete, the resultant dark solution was warmed to reflux and stirred at that temperature for 18 hours. The solution was cooled to ambient temperature, concentrated in vacuo and the residue obtained was chromatographed on silica gel (eluting with 25% EtOAc/hexanes) to afford BK1114 as a colorless oil (~1:1 mixture of C5 diastereomers, 26 mg, 30% yield).

Variations of the aforementioned procedures are available to provide analogs. For example, replacing 3-hydroxy-3-methyl-1-decene with allylic alcohol 6 in the cross-metathesis with 2 will provide a product whose alkyne protecting group can be removed by oxidative decomplexation to afford 7. Further variations of 7 wherein the alkyne unit occupies other positions within the hydrocarbon chain are similarly accessible.

Variations of the aforementioned procedures are available to provide analogs. For example, replacing 3-hydroxy-3-methyl-1-decene with allylic alcohol 8 in the cross-metathesis with 2 will provide product 9.

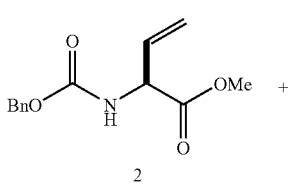

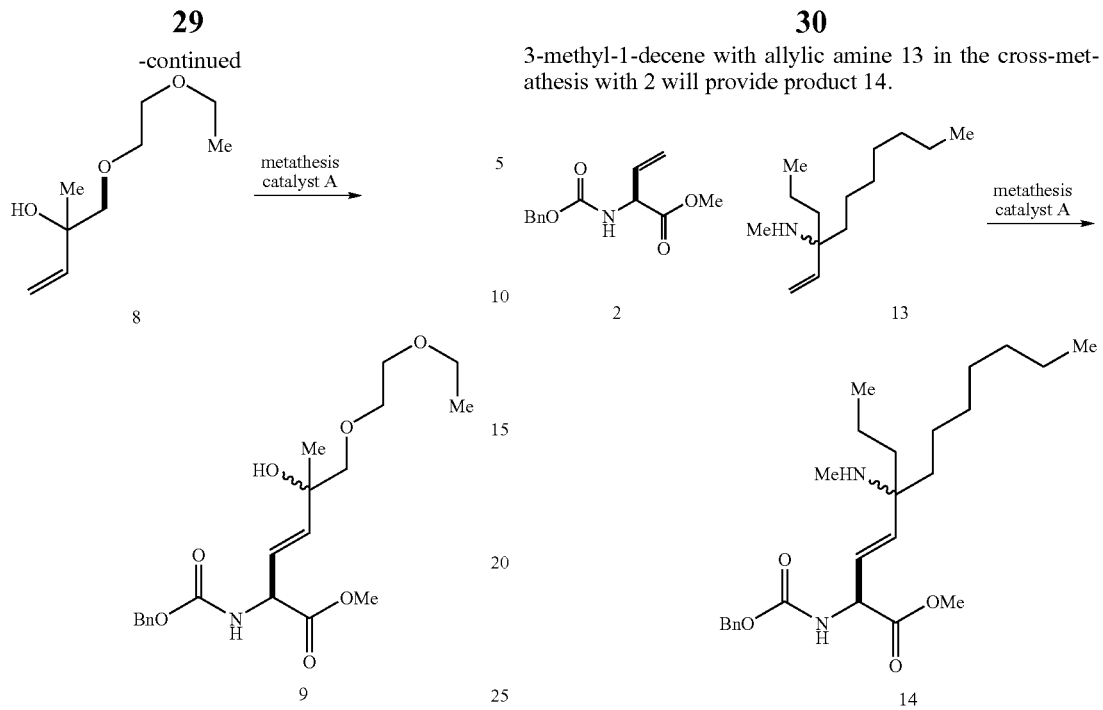

Variations of the aforementioned procedures are used to provide further analogs. For example, cross-methathesizing heterocycle 10 with fluorinated allylic alcohol 11 will provide product 12.

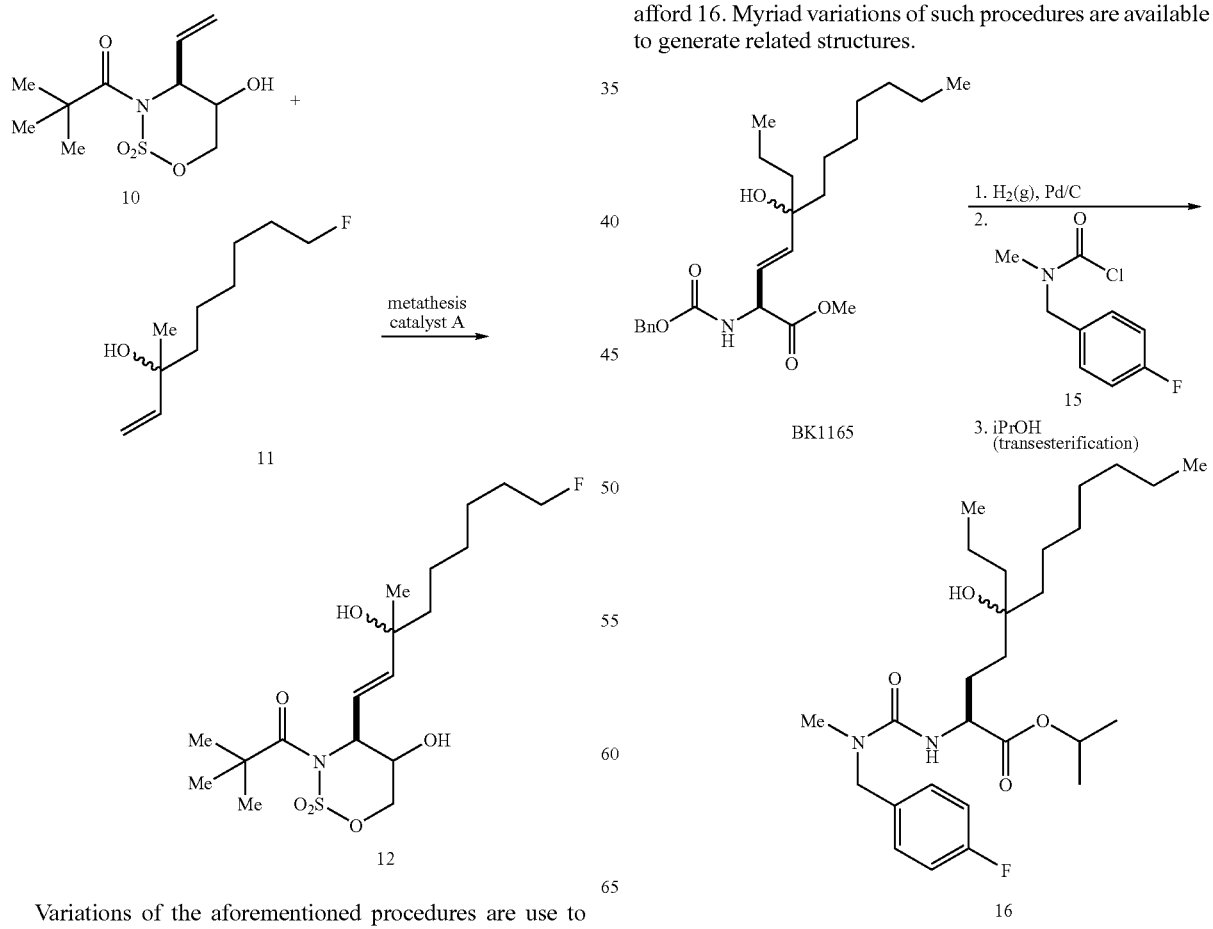

Variations of the aforementioned procedures are use to provide further analogs. For example, replacing 3-hydroxy-3-methyl-1-decene with allylic amine 13 in the cross-metathesis with 2 will provide product 14.

BK1165 can be manipulated to produce additional analogs. For example, hydrogenolysis in the presence of catalytic amounts of palladium on carbon, treating the incipient amine with carbamoyl chloride 15 followed by dissolution in isopropanol in the presence of a transesterification catalyst will afford 16. Myriad variations of such procedures are available to generate related structures.

TABLE 1
Structures of additional, exemplary active analogs.
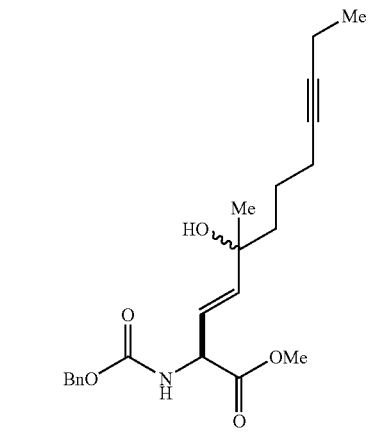
7
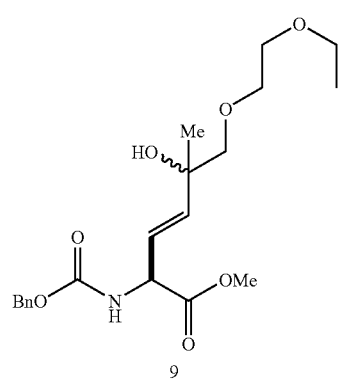
9
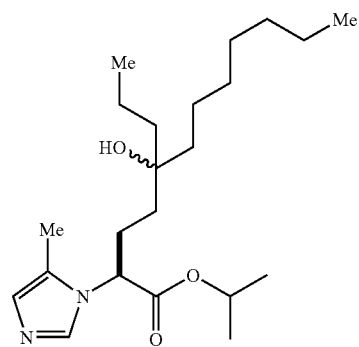
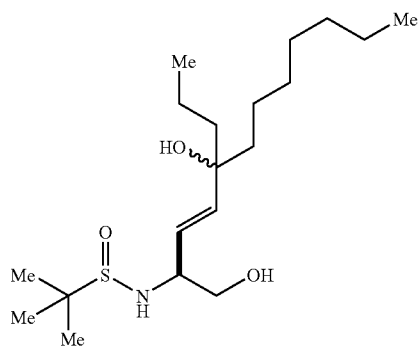
TABLE 1-continued
Structures of additional, exemplary active analogs.
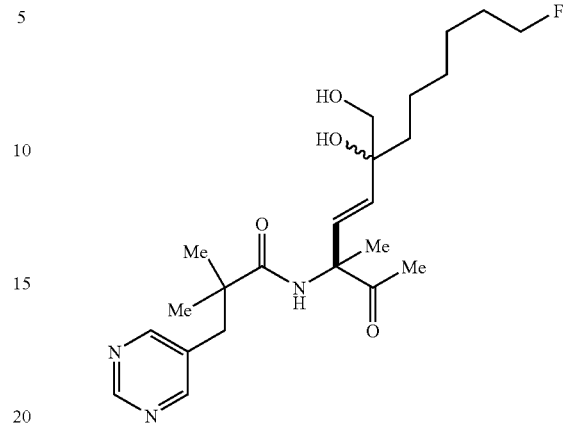
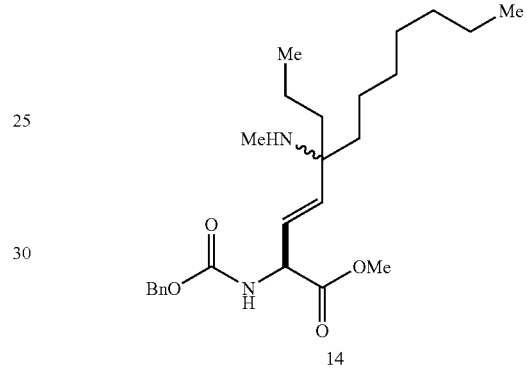
14
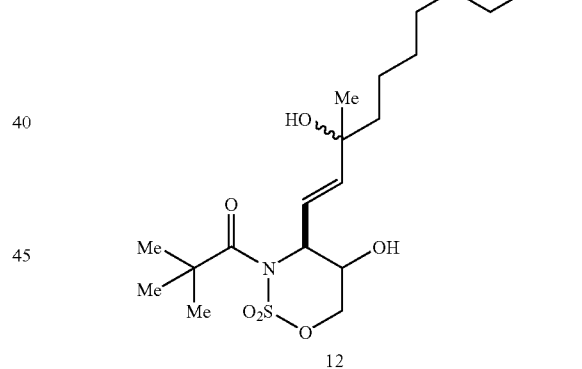
12
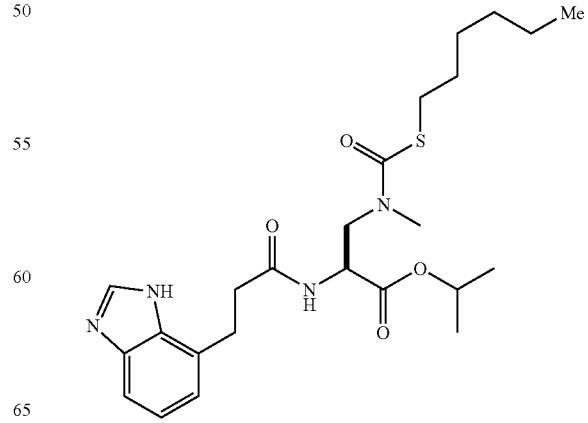

TABLE 1-continued

Structures of additional, exemplary active analogs.

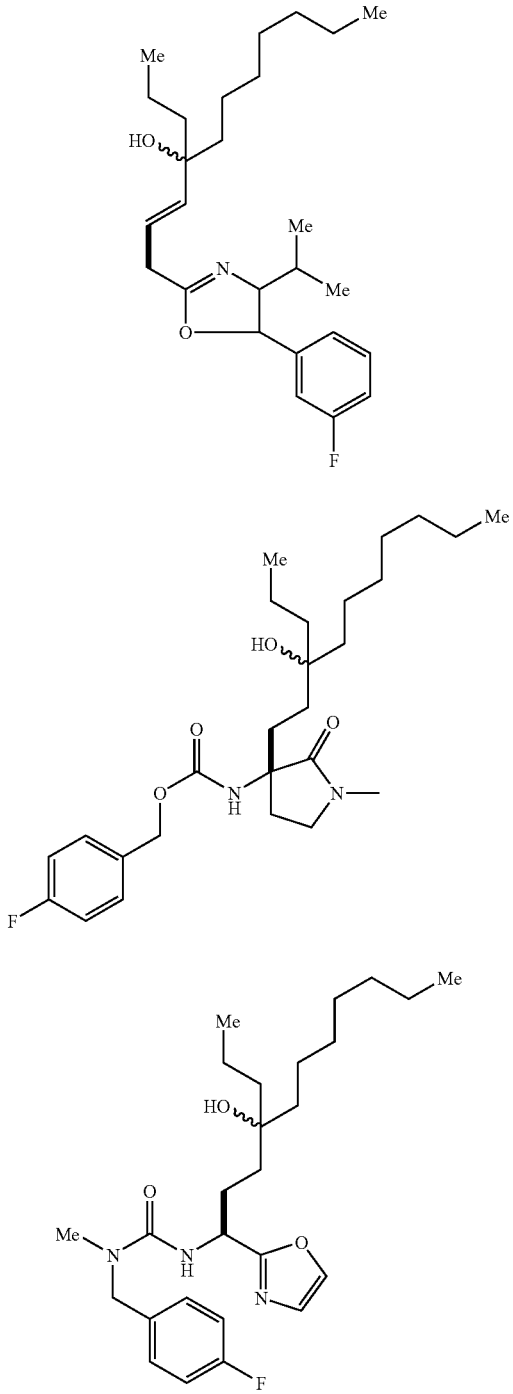

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A pharmaceutical composition comprising a ghrelin O-acyltransferase (GOAT) inhibitor of the structure 1:

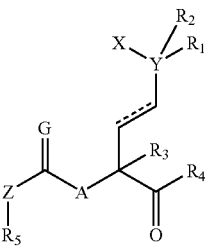

wherein:
$R_1$, is selected from unsubstituted n-heptanyl, unsubstituted n-heptenyl, unsubstituted n-heptynyl and unsubstituted methyl-diethylene glycol (—$CH_2OCH_2CH_2OCH_2CH_3$);
$R_2$-$R_5$ are independently selected from hydrogen, optionally hetero-, optionally substituted alkyl, optionally hetero-, optionally substituted alkenyl, optionally hetero-, optionally substituted alkynyl, optionally hetero-, optionally substituted aryl, and an optionally substituted heteroatom;
A is selected from NH, and N-alkyl;
G is O;
X is selected from hydroxyl, amino, alkylamino, and alkylthio;
Y is C; and
Z is selected from O, S, NH and N-alkyl,
or a pharmaceutically acceptable salt thereof, and a pharmaceutically acceptable excipient, wherein said inhibitor inhibits said ghrelin O-acyltransferase (GOAT), and said composition is suitable for pharmaceutical use.

2. The composition of claim 1, wherein $R_1$, is selected from n-heptanyl, n-heptenyl, and n-heptynyl.

3. The composition of claim 1, wherein $R_1$, is n-heptanyl.

4. The composition of claim 1, wherein $R_1$, is n-4-heptenyl (—$CH_2CH_2CH_2CHCHCH_2CH_3$).

5. The composition of claim 1, wherein $R_1$, is n-4-heptynyl.

6. The composition of claim 1 wherein $R_1$ is methyl-diethylene glycol (—$CH_2OCH_2CH_2OCH_2CH3$).

7. The composition of claim 1 wherein $R_2$ is H or optionally substituted, lower (C1-C5) alkyl.

8. The composition of claim 1 wherein $R_2$ is methyl, ethyl, propyl or butyl.

9. The composition of claim 1 wherein $R_3$ is H or optionally substituted, lower (C1-C5) alkyl.

10. The composition of claim 1 wherein $R_3$ is H, methyl, ethyl, propyl or butyl.

11. The composition of claim 1 wherein $R_4$ is methoxy.

12. The composition of claim 1 wherein $R_4$ is the structure 2:

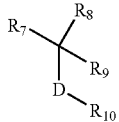

wherein:
$R_4$ is the point of attachment and is selected from a bond, optionally substituted lower alkyl, NH, S and O;

$R_8$ and $R_9$ are independently selected from hydrogen and optionally hetero-, optionally substituted alkyl; and D is selected from $CH_2$ and NH, and $R_{10}$ is a 5-7 membered, optionally heterocyclic ring.

13. The composition of claim 12 wherein $R_8$ is H and $R_9$ is methoxymethyl (—$CH_2OCH_3$).

14. The composition of claim 1 wherein $R_5$ is $R_6(CH_2)_n$ wherein $R_6$ is a 5-7 membered, optionally heterocyclic ring, and n is an integer from 0 to 5.

15. The composition of claim 1 wherein $R_5$ is benzyl.

16. A pharmaceutical composition comprising a ghrelin O-acyltransferase (GOAT) inhibitor or a pharmaceutically acceptable salt thereof, wherein said inhibitor is selected from the group consisting of:

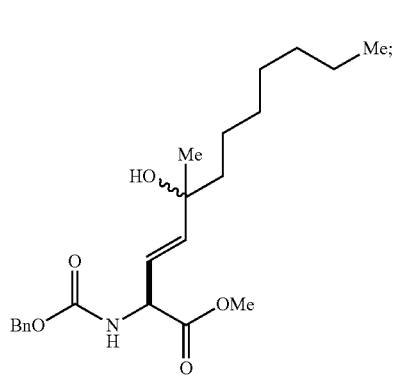

BK1114

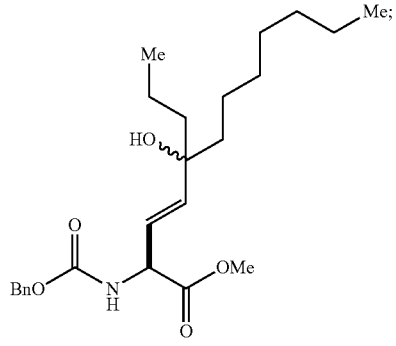

BK1165

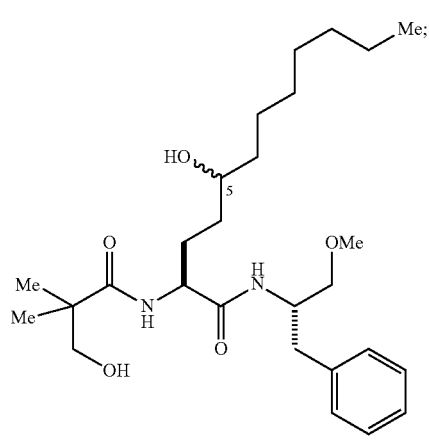

PH-1152

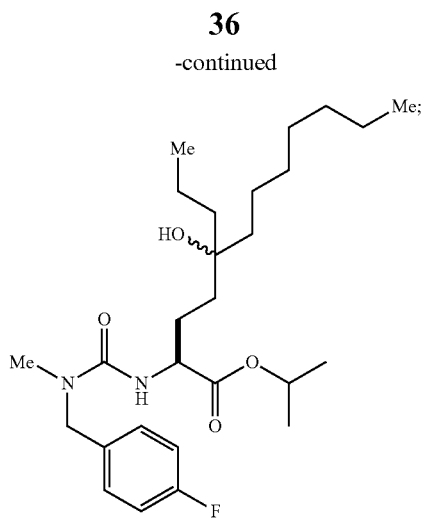

16

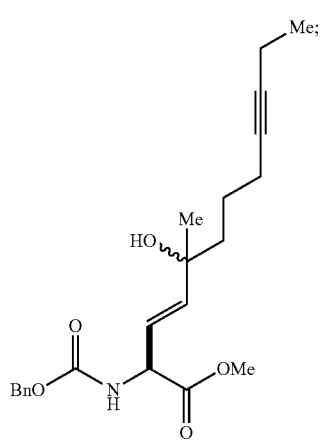

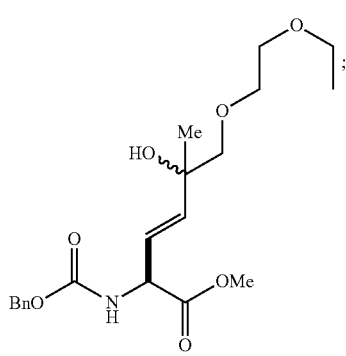

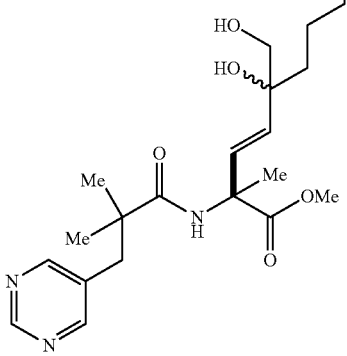

F; and

-continued

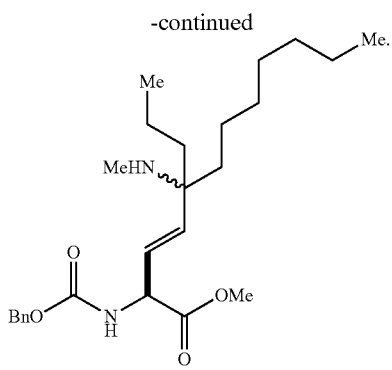

17. A method of inhibiting ghrelin O-acyltransferase (GOAT), comprising the steps of contacting the GOAT with the composition of claim 1, and detecting a resultant inhibition of the GOAT.

18. The composition of claim 1 in unit dosage form.

19. The composition of claim 1 in unit dosage form having the inhibitor in an amount from 1 to 1000 mg.

20. The composition of claim 1 in unit dosage form contained in a prefilled, premeasured ampule or syringe, or in a pill, tablet, capsule, or lozenge.

21. The composition of claim 1 in unit dosage form having the inhibitor in an amount from 1 to 1000 mg, and contained in a prefilled, premeasured ampule or syringe.

22. The composition of claim 1 in unit dosage form having the inhibitor in an amount from 1 to 1000 mg, and contained in a pill, tablet, capsule, or lozenge.

23. The composition of claim 1 co-formulated with an additional active ingredient selected from the group consisting of (i) an appetite-suppressant or antiobesity drug; (ii) an antidiabetic drug; and (iii) a cholesterol-modulating drug.

24. The composition of claim 1 co-formulated with an additional active ingredient selected from the groups consisting of orlistat, sibutramine, metformin, exenatide, pramlintide acetate, rimonabant, insulin, glipizide, glyburide, glimepiride, gliclazide, repaglinide, nateglinide, rosiglitazone, pioglitazone, miglitol, acarbose, incretin mimetics, liraglutide, gastric inhibitory peptide (GIP) analog, vildagliptin, sitagliptin, amylin analogue, and HMG-CoA reductase inhibitor.

* * * * *